United States Patent [19]
Jarin

[11] Patent Number: 4,773,637
[45] Date of Patent: Sep. 27, 1988

[54] EXAMINATION TABLE WITH LONGITUDINALLY MOVABLE TOP

[75] Inventor: Jean P. Jarin, Lamorlaye, France
[73] Assignee: Thomson-CGR, Paris, France
[21] Appl. No.: 940,086
[22] Filed: Dec. 10, 1986
[30] Foreign Application Priority Data Dec. 13, 1985 [FR] France ............... 85 18531

[51] Int. Cl.⁴ ........................... A61G 13/00
[52] U.S. Cl. ................................ 269/322
[58] Field of Search .............. 269/322–328; 378/17, 209

[56] References Cited

U.S. PATENT DOCUMENTS 3,397,411 8/1968 Rossi ................. 269/322
4,475,072 10/1984 Schwehr et al. ............. 318/602

FOREIGN PATENT DOCUMENTS 0015612 2/1980 European Pat. Off. .
0097086 6/1983 European Pat. Off. .

Primary Examiner—Frederick R. Schmidt
Assistant Examiner—Judy J. Hartman
Attorney, Agent, or Firm—Oblon, Fisher, Spivak, McClelland & Maier

[57] ABSTRACT

The invention pertains to an examination table, the top of which can be moved along its longitudinal axis on at least one roller. The top is moved, in relation to a pedestal, by a driving shaft which is set along one and the same crosswise axis as the roller.

14 Claims, 3 Drawing Sheets

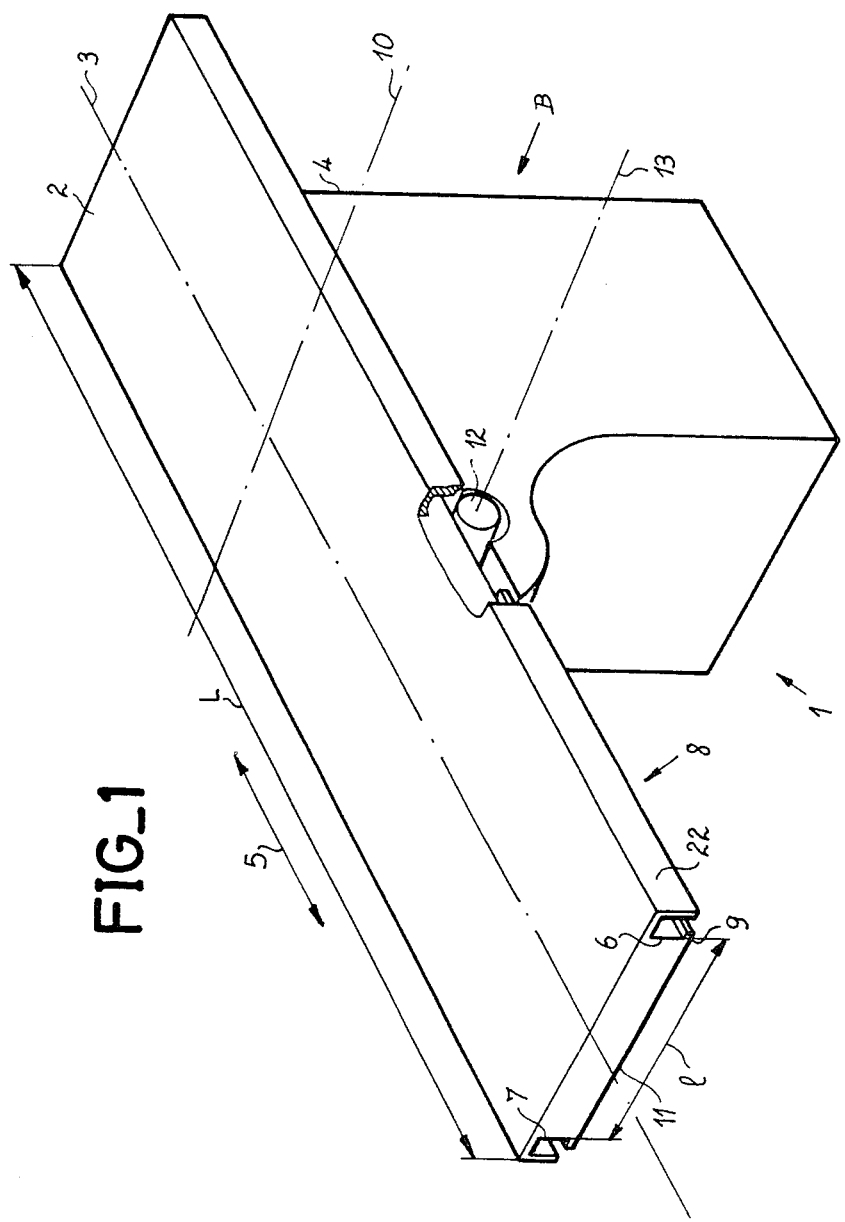
FIG_1

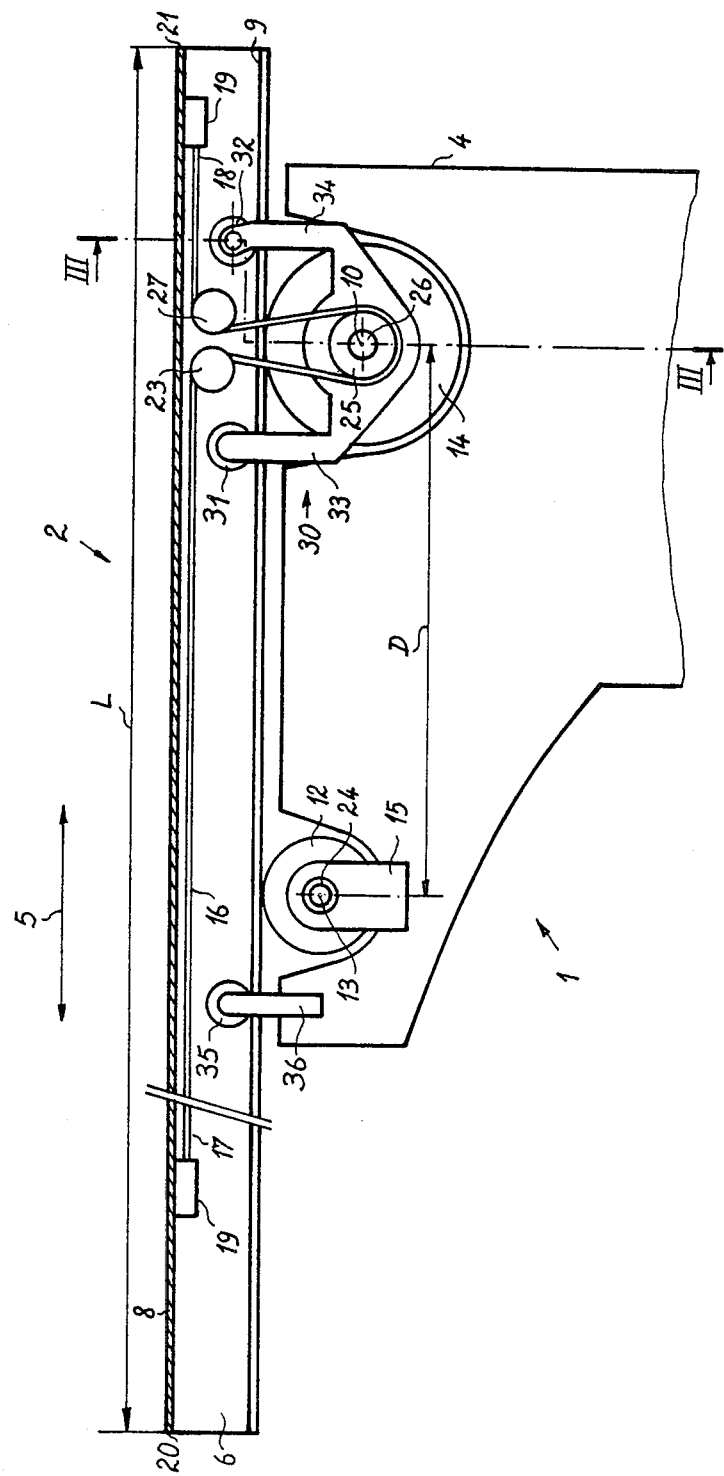
FIG_2

FIG_3
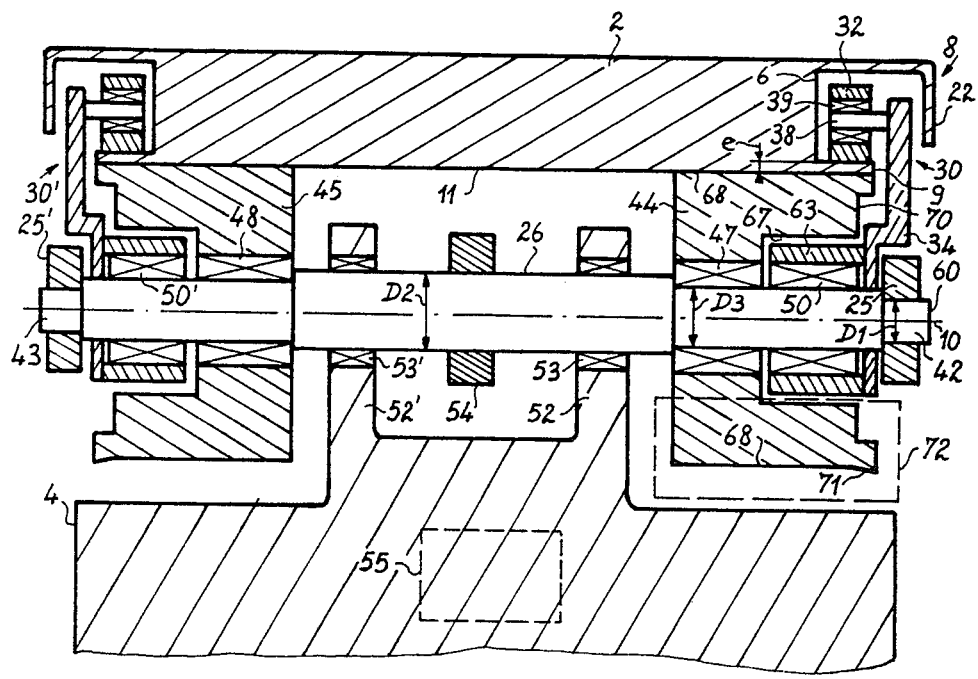
FIG_4
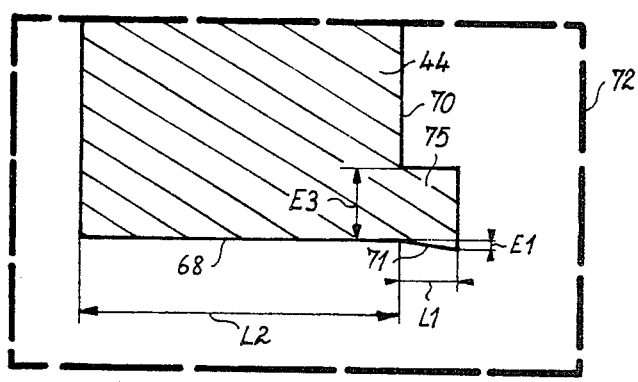

EXAMINATION TABLE WITH LONGITUDINALLY MOVABLE TOP

FIELD OF THE INVENTION

The present invention pertains to an examination table the patient-supporting top of which can be made to move along its longitudinal axis. The invention especially pertains to a lay-out of means used to achieve this motion.

BACKGROUND OF THE INVENTION

In X-ray examination tables, it is common to make a patient-supporting table top move in relation to a fixed element such as the pedestal of the examining table, for example. The motion is generally got through actuation by driving means, which are integrally joined to the pedestal, the rotational movement of these driving means being transformed into a linear movement which is transmitted to the table top by a system of pulleys and belts. In general, a driving shaft is made to rotate on its axis and, by means of at least one cogged wheel, it drives one or more belts the ends of which are fixed to the table top which has to be moved. The belts move about against different pulleys, and the motion of the belts drives the motion of the table top.

The table top is moved on supporting means such as, for example, firstly, an element that is mobile along the longitudinal axis and fixed to one end of the table top, and, secondly, a roller set under the table top along an axis which is crosswise to the length of the table top. These supporting means may also comprise supporting rollers only, set along axes which are crosswise to the length of the table top, at least two supporting rollers being needed if their length substantially corresponds to the width of the table top. Furthermore, reaction rollers must be set on the longitudinal sides of the table top, in reaction to each roller.

These various pulleys, various rollers and various reaction rollers are held by supporting shafts which are integrally joined with the fixed part of the table—i.e., with the pedestal.

One of the problems raised by these supporting shafts, owing to their number, is the fact that, as a result of their careful distribution, the pedestal acquires a large dimension parallel to the longitudinal axis of the table top. This large dimension of the pedestal constitutes, in most cases, an irksome feature, especially in examination tables with movable table tops where, firstly, there has to be easy access to the patient and, secondly, the maximum amount of space must be left unoccupied for setting up the various X-ray instruments.

Moreover, the proliferation of these supporting shafts considerably increases the cost of the examination table.

SUMMARY OF THE INVENTION

The present invention pertains to an examination table the patient-supporting table top of which can be moved along its longitudinal axis. The means used to achieve this motion are arranged in a new form of lay-out which reduces the number of these means and their bulk while, at the same time, preserving the qualities of motion of the table top.

The present invention is an examination table comprising a longitudinally movable table top, a pedestal, supporting means that bear the table top, and a driving shaft fixed to the pedestal and working together with means of movement to move the table top along its longitudinal axis with respect to the pedestal. The supporting means comprise at least one roller and at least one reaction device. The driving shaft is set along an axis crosswise to the longitudinal axis, and the roller is set along the crosswise axis. The roller is borne by the driving shaft by at least one bearing means.

BRIEF DESCRIPTION OF THE DRAWINGS

The invention will be better understood from the following description, which is given as a non-exhaustive example, along with the four appended figures, of which:

FIG. 1 gives a perspective of the general configuration of an examination table according to the invention;

FIG. 2 depicts a side view of the examination table, along an arrow B shown in FIG. 1, in such a way as to depict an examination table top lengthwise;

FIG. 3 gives a cross-section view of the examination table along the arrows III—III shown in FIG. 2;

FIG. 4 depicts a portion of a roller depicted in a box in FIG. 3.

DETAILED DESCRIPTION OF THE INVENTION

FIG. 1 gives a perspective of the general configuration of an examination table according to the invention.

The examination table 1 comprises a table top 2 designed to support a patient. The table top 2 can be moved along its longitudinal axis 3, as shown by an arrow 5, in relation to a pedestal 4, using means of motion which are not depicted in FIG. 1. These means of motion comprise, especially, a driving shaft set along a first axis 10 which is crosswise to the length of the table top 2.

In the non-exhaustive example described, the table top 2 comprises, on its first and second longitudinal sides 6,7, a shielding channel 8 under which there extends, along the length L of the table top 2, a flat edge 9 which goes over the width l of the table top 2, the channel 8 comprising an edge 22 curved towards a lower side 11 of the table top 2. The flat edge 9 is substantially in the plane of the lower edge 11 of the table top 2 and constitutes a bearing surface, as will be explained in greater detail in a subsequent part of the description.

According to one characteristic of the invention, supporting means of the table top 2 comprise a support formed of at least one first roller 14 (not depicted in FIG. 1) set along the same first axis 10, which is crosswise to the table top 2, as the driving shaft described earlier. In the non-exhaustive example described, the supporting means further comprise at least one second roller 12 set along a second axis 13 which is parallel to the first axis 10, an end of the second roller 12 being depicted in FIG. 1 through an opening made in the drawing of the channel 8 and of the flat edge 9.

FIG. 2 depicts a side view of the examination table 1 along the arrow B depicted in FIG. 1, in such a way as to partially represent the table top 2 along its length L, on its first longitudinal side 6. The edge 22 of the channel 8 is not depicted.

As mentioned earlier, the table top 2 is partially supported by at least one first roller 14 set along the first axis 10 and comprising, for example, only one roller or several rollers. The table top 2 is further supported by at least one second support comprising at least one second roller 12. In the non-exhaustive example described, the second roller 12 has, perpendicular to the plane of the figure, a length (not depicted) which is substantially equal to the previously mentioned width l of the table top 2, but which may also comprise, according to a standard practice, two rollers of smaller length set on the same second axis 13. One of these rollers may, for example, be closer to the first longitudinal side 6, and the other roller may be closer to the second longitudinal side 7. The second roller 12 is of a type known in the prior art, and it is mounted in a conventional way on a supporting shaft 24 so that it is movable rotationally on the second axis 13 while being integrally joined by supporting arms 15 to its ends which are opposite to the pedestal 4.

In the non-exhaustive example of the description, the means of motion used to move the table top 2 along its longitudinal axis 3 comprise at least one belt 16. The first and second ends 17, 18 of the belt 16 are respectively fixed, by conventional fixing means 19, on a first end 20 side and a second end 21 side of the table top 2. The fixings 19 are joined to the table top 2, in the channel 8 for example. The belt 16 is laid in the part shielded by the channel 8 and, starting from its first end 17, it extends along the table top 2 until it turns around a first pulley 23 mounted so as to rotate freely. After the first pulley 23, the belt 16 is sent on in a substantially opposite direction to that of the plane of the table top 2 until it turns around a first cogged wheel 25 mounted on a driving shaft 26. The belt 16 then returns to the plane of the table top 2 and turns around a second pulley 27 which is substantially aligned with the first pulley 23 along the direction of the length L of the table top 2. The belt 16 turns around the second pulley 27 and extends in the direction of the second end 21 of the table top 2, where it is fixed to the fixing means 19. A similar assembly can be made for the second longitudinal side 7 (not depicted) of table top 2.

During operation, the driving shaft 26 is made to rotate on itself around the first axis 10, using conventional driving means (not depicted) set, for example, in the pedestal 4. Since the first cogged wheel 25 is fixed to the driving shaft 26, it gives rise to the motion of the belt 16 which itself causes the table top 2 to move along its longitudinal axis 3 in either one of the directions represented by the arrow 5, depending on the direction in which the driving shaft 26 rotates.

As will be explained in greater detail in a part of the description pertaining to FIG. 3, the first roller 14 supports the table top 2 along the same first crosswise axis 10 as the axis along which the driving shaft 26 is set. The motion of the table top 2, supported on the rollers 12, 14, causes these rollers to rotate on their axes 13, 10. In order to make the rotation of the first roller 14 independent of the rotation of the driving shaft 26, the first roller 14 is mounted on the driving shaft 26 by a bearing means (not depicted in FIG. 2). Thus, in addition to performing its function of actuating the motion of the table top 2, the driving shaft 26 constitutes a supporting shaft for the first roller 14 and, if necessary, a support for other means designed to maintain a fixed position with respect to the pedestal 4.

The reaction to the thrust of the first roller 14 on the table top 2 is exerted by a first roller reaction device 30. In the non-exhaustive example described, the first roller reaction device 30 comprises a first roller 31 and a second roller 32, set on either side of the first pulley 23 and the second pulley 27 and supported on the flat edge 9 on which they roll when the table top 2 is in motion. The first and second rollers 31, 32 are respectively borne by a first arm 33 and a second arm 34.

In this configuration, the first roller 31 and the second roller 32 each provides the most efficient possible reaction to the first roller 14. The first roller 31 and the second roller 32 are set symmetrically on either side of the first roller 14, and in this configuration, it is worthwhile for the first roller reaction device 30 to be borne by a supporting shaft set along the first axis 10.

To this end, according to one characteristic of the invention, the first roller reaction device 30 is mounted on the driving shaft 26 through second bearing means (not depicted) so that they do not depend on the rotation of the driving shaft 26.

It is seen that this arrangement avoids the use of an additional supporting shaft for the first roller 14 and another additional supporting shaft for the first roller reaction device 30. This makes it possible, especially, to obtain as small a distance D as possible between the first axis 10 of the first roller 14 and the second axis 13 of the second roller 12, while taking into account the fact that the distance D should have a minimum value if the table top 2 is to be properly supported. The fitting of an additional shaft support to carry, for example, the first roller 14, would have led to increasing the dimension of the pedestal 4 parallel to the longitudinal axis 3.

In the non-exhaustive example described, a third roller 35 is borne by a strap 36 fixed to the pedestal 4 near the second roller 12 in order to balance the thrust of the latter.

FIG. 3 depicts a cross-section view of the examination table 1 along the arrows III—III depicted in FIG. 2.

The driving shaft 26 is set under the table top 2 along the first axis 10, with its first and second ends 42, 43, going beyond the flat edge 9.

In the non-exhaustive example of the description, the first roller 14 comprises a first end roller 44 and a second end roller 45, respectively borne by the first end 42 and the second end 43 of the driving shaft 26 and, respectively, by a first bearing means 47 and a second bearing means 48. The first roller reaction device 30 and a second roller reaction device 30' are also mounted on the driving shaft 26, at the first end 42 and the second end 43 respectively of this driving shaft, the first and second roller reaction devices 30, 30' being mounted on the driving shaft 26 through a third bearing means 50 and a fourth bearing means 50' respectively. Finally, the ends 42, 43, as such, of the driving shaft 26 are occupied by the first cogged wheel and a second cogged wheel 25, 25' mounted so as to be integrally joined to the driving shaft 26 and so as to rotate with this driving shaft. Each cogged wheel drives the motion of a belt 16 (not depicted in FIG. 3) as explained previously.

The driving shaft 26 is integrally joined to the pedestal 4 in a manner known in the prior art. The pedestal 4 comprises, for this purpose, a first upright 52 and a second upright 52' to which the driving shaft 26 is fixed by a fifth bearing means 53 and a sixth bearing means 53' so as to provide for its rotation. In the non-exhaustive example described, the driving shaft 26 comprises, in a central portion of its length, a third cogged wheel 54 by which it is made to rotate under the effect of a driving means 55 symbolized by a rectangle drawn with dashes. The driving means 55 are, for example, contained in the pedestal 4 and work together with the third cogged wheel 54 by means of a belt, for example, (not depicted), to make the driving shaft 26 rotate.

The following description specifies the assembly that has just been described, solely with reference to the first end 42 of the driving shaft 26. However, the exaple is also valid for the second end 43, these assemblies being symmetrical.

Starting from the first end 42, the first cogged wheel 25 is mounted on the driving shaft 26 on an end part 60 of the driving shaft 26. In the non-exhaustive example described, the end part 60 has an first diameter D1 which is smaller than the second diameter D2 of the driving shaft 26 in its central portion. Going towards the interior of the table top 2, we then find the third bearing means 50 mounted on the driving shaft 26 on a part of this shaft having a third diameter D3, which is between the first diameter D1 and the second diameter D2. The third bearing means 50 is integrally joined to the first roller reaction device 30, of which FIG. 3 depicts the second arm 34 bearing the second roller 32 in a deeper plane than that of the figure. The second roller 32 is integrally joined to the second arm 34 by means of a shaft 38 and a bearing 39. The second arm 34 is set along a substantially vertical plane between an external edge of the flat edge 9 and the edge 22 of the shielding channel 8. The second arm 34 is integrally joined to the third bearing means 50 by a part 63, the third bearing means 50 being set on a part of the driving shaft 26 which is located so that it substantially faces the flat edge 9—i.e., it is further towards the interior of the table top 2. We then find the first bearing means 47 through which the first end roller 44 is borne by the driving shaft 26.

The first end roller 44 comprises a central cavity 67 which is open, on a side 70 pointed towards the first end 42 of the driving shaft 26, so as to contain the third bearing means 50 and the part 63 by which the latter is fixed to the second arm 34 and the first arm 33 (not depicted in FIG. 3). This makes it possible to give the first end roller 44 a bearing surface 68 which is supported on the lower side 11 of the table top 2 and on the flat edge 9, between this flat edge and the part 63, so as to support the table top 2 substantially beneath the first longitudinal side 6 where it has its greatest rigidity and beneath the flat edge 9 on which the reaction of the second roller 32 is exerted.

The first end roller 44 is made of a conventional material, such as a polyurethane-based material for example, which gives it adequate mechanical rigidity as well as a degree of flexibility, especially to compensate for any variations in the thickness e of the flat edge 9.

The variations in the thickness e of the flat edge 9, considered in the direction of increasing thickness, tend to hamper the movement of the table top 2 and may, in extreme cases, cause it to be jammed. Again, the lessening of the thickness e may cause the table top 2 to be unstable in directions perpendicular to its plane.

Most of these flaws are avoided through the flexibility of the end rollers 44, 45. However, small decreases in the thickness e, although absorbed by the end roller 44, 45, especially by that part of the bearing surface 68 which faces the flat edge 9, tend to diminish the thrust exerted by the end roller 44, 45 on the table top 2 which, at that point, is no longer maintained with maximum efficiency. This tends to reduce the quality of the motion of the table top 2 and to give a disagreeable feeling of instability during handling. In the invention, to avoid these effects, each of the end rollers 44, 45, has, on its bearing surface 68, a lip 71 forming an additional thickness which tends to be crushed in varying degrees depending on variations in the thickness of the flat edge 9. The lip 71 is supported on the flat edge 9.

FIG. 4 depicts a part of the first end roller 44 which is in a box 72 depicted in FIG. 1. The box 72 and contains the lip 71, which can thus be described in greater detail with reference to FIG. 4.

In the non-exhaustive example described, the lip 71 extends the bearing surface 68 towards the side 70 and comprises a second thickness e1 forming an additional, gradually increasing thickness. In the non-exhaustive example described, the lip 71 is made of the same material as the first end roller 44 so that it can be obtained, in an example of manufacture, when making the first end roller 44. The lip 71 can be included in the length of the bearing surface 68 or, as in the non-exhaustive example described, it can constitute an additional length L1 so as to form, on the side 70 of the first end roller 44, an additional part 75, of which a third thickness e3, considered along a plane perpendicular to the plane of the table top 2, makes it possible to obtain the desired flexibility of the lip 71 more efficiently.

It is indicated, by way of a non-exhaustive example, that for a flat edge 9, of which the dimension parallel to the first axis 10 is approximately 20 mm., the lip 71 has an additional length of about 10 mm. and a thickness e1 of about 1 mm., and that the third thickness e3 is about 10 mm., the length L2 of the bearing surface 68 being substantially equal to 70 mm.

This description is a non-exhaustive example which shows how to use a driving shaft to support elements which are normally independent of this driving shaft so as to avoid the proliferation of the supporting shafts needed to support these elements, thus making it possible to build an examination table which is more compact and costs less than in the prior art.

What is claimed is:

1. An examination table comprising:
   (a) a table top having a longitudinal axis;
   (b) a pedestal;
   (c) a driving shaft mounted in said pedestal for rotation about a first axis perpendicular to the longitudnal axis of said table top;
   (d) first means for rotating said driving shaft;
   (e) at least one first roller mounted on said driving shaft for rotation independently of the rotation of said driving shaft, said at least one first roller being sized, shaped, and positioned to support said table top;
   (f) at least one second roller mounted on said pedestal for rotation about a second axis perpendicular to the longitudinal axis of said table top and spaced from the first axis in the longitudinal direction of said table top, said at least one second roller being sized, shaped, and positioned to support said table top;
   (g) at least one third roller mounted on said pedestal for rotation about a third axis perpendicular to the longitudinal axis of said table top and spaced from the first axis in the longitudinal direction of said table top on the side of the first axis away from the second axis, said at least one third roller being sized, shaped, and positioned to run on a first upwardly directed surface on said table top, thereby supporting reaction forces from said at least one first roller;
   (h) at least one fourth roller mounted on said pedestal for rotation about a fourth axis perpendicular to the longitudinal axis of said table top and spaced from the second axis in the longitudinal direction of said table top on the side of the second axis away from the first axis, said at least one fourth roller being sized, shaped, and positioned to run on a second upwardly directed surface of said table top, thereby supporting reaction forces from said at least one second roller; and
(i) second means for transmuting the rotary motion of said driving shaft into linear motion of said table top parallel to its longitudinal axis,
wherein:
(j) said at least one first roller has an axial side and a central cavity open to said axial side;
(k) said at least one third roller is mounted on a first arm;
(l) said first arm is mounted on a first bearing means; and
(m) said first bearing means is mounted on said driving shaft and at least partially received in said central cavity.

2. An examination table as recited in claim 1 wherein said first and second upwardly directed surfaces are the same surface.

3. An examination table as recited in claim 1 wherein said second means comprise:
(a) at least one cogged wheel mounted on said driving shaft for rotation therewith and
(b) a belt trained over said at least one cogged wheel and having a first end attached to said table top at a first point and a second end attached to said table top at a second point spaced from said first point in the longitudinal direction of said table top.

4. An examination table as recited in claim 3 wherein:
(a) said second means further comprise:
(i) a first pulley mounted on said table top for rotation about a fifth axis perpendicular to the longitudinal axis of said table top and spaced from the first axis in the longitudinal direction of said table top on the side of the first axis toward the second axis and
(ii) a second pulley mounted on said table top for rotation about a sixth axis perpendicular to the longitudinal axis of said table top and spaced from the first axis in the longitudinal direction of said table top on the side of the first axis away from the second axis;
(b) said belt is trained over said first pulley between said first point and said at least one cogged wheel; and
(c) said belt is trained over said second pulley between said second point and said at least one cogged wheel.

5. An examination table as recited in claim 1 and further comprising at least one fifth roller mounted on said pedestal for rotation about a seventh axis perpendicular to the longitudinal axis of said table top and spaced from the first axis in the longitudinal direction of said table top on the side of the first axis toward the second axis, said at least one fifth roller being sized, shaped, and positioned to run on a third upwardly directed surface of said table top, thereby supporting reaction forces from said at least one first roller.

6. An examination table as recited in claim 5 wherein said first, second, and third upwardly directed surfaces are the same surface.

7. An examination table comprising:
(a) a table top having a longitudinal axis;
(b) a pedestal;
(c) a driving shaft mounted in said pedestal for rotation about a first axis perpendicular to the longitudinal axis of said table top;
(d) first means for rotating said driving shaft;
(e) at least one first roller mounted on said driving shaft for rotation independently of the rotation of said driving shaft, said at least one first roller:
(i) being sized, shaped, and positioned to support said table top and
(ii) having a radially outwardly projecting flexible lip to compensate for irregularities in the surface of said table top on which it runs;
(f) at least one second roller mounted on said pedestal for rotation about a second axis perpendicular to the longitudinal axis of said table top and spaced from the first axis in the longitudinal direction of said table top, said at least one second roller being sized, shaped, and positioned to support said table top;
(g) at least one third roller mounted on said pedestal for rotation about a third axis perpendicular to the longitudinal axis of said table top and spaced from the first axis in the longitudinal direction of said table top on the side of the first axis away from the second axis, said at least one third roller being sized, shaped, and positioned to run on a first upwardly directed surface of said table top, thereby supporting reaction forces from said at least one first roller;
(h) at least one fourth roller mounted on said pedestal for rotation about a fourth axis perpendicular to the longitudinal axis of said table top and spaced from the second axis in the longitudinal direction of said table top on the side of the second axis away from the first axis, said at least one fourth roller being sized, shaped, and positioned to run on a second upwardly directed surface of said table top, thereby supporting reaction forces from said at least one second roller; and
(i) second means for transmuting the rotary motion of said driving shaft into linear motion of said table top parallel to its longitudinal axis.

8. An examination table as recited in claim 7 wherein the thickness of said radially outwardly projecting flexible lip increases in the direction toward the adjacent end of said driving shaft.

9. An examination table as recited in claim 7 wherein said radially outwardly projecting flexible lip extends from the remainder of said at least one first roller in the direction toward the adjacent end of said driving shaft.

10. An examination table as recited in claim 7 wherein said first and second upwardly directed surfaces are the same surface.

11. An examination table as recited in claim 7 wherein said second means comprise:
(a) at least one cogged wheel mounted on said driving shaft for rotation therewith and
(b) a belt trained over said at least one cogged wheel and having a first end attached to said table top at a first point and a second end attached to said table top at a second point spaced from said first point in the longitudinal direction of said table top.

12. An examination table as recited in claim 11 wherein:
(a) said second means further comprise:
(i) a first pulley mounted on said table top for rotation about a fifth axis perpendicular to the longitudinal axis of said table top and spaced from the first axis in the longitudinal direction of said table top on the side of the first axis toward the second axis and (ii) a second pulley mounted on said table top for rotation about a sixth axis perpendicular to the longitudinal axis of said table top and spaced from the first axis in the longitudinal direction of said table top on the side of the first axis away from the second axis;

(b) said belt is trained over said first pulley between said first point and said at least said one cogged wheel; and (c) said belt is trained over said second pulley between said second pulley and said at least one cogged wheel.

13. An examination table as recited in claim 7 and further comprising at least one fifth roller mounted on said pedestal for rotation about a seventh axis perpendicular to the longitudinal axis of said table top and spaced from the first axis in the longitudinal direction of said table top on the side of the first axis towards the second axis, said at least one fifth roller being sized, shaped, and positioned to run on a third upwardly directed surface on said table top, thereby supporting reaction forces from said at least one first roller.

14. An examination table as recited in claim 13 wherein said first, second, and third upwardly directed surfaces are the same surface.

* * * * *